(12) United States Patent
Jang et al.

(10) Patent No.: US 10,456,350 B2
(45) Date of Patent: Oct. 29, 2019

(54) EYE MAKE-UP COSMETIC COMPOSITION WITH EXCELLENT CURLING HOLDING FORCE

(71) Applicant: AMOREPACIFIC CORPORATION, Seoul (KR)

(72) Inventors: Soon Hui Jang, Yongin-si (KR); Eun Sil Han, Yongin-si (KR)

(73) Assignee: AMOREPACIFIC CORPORATION, Yongsan-Gu, Seoul (KR)

( * ) Notice: Subject to any disclaimer, the term of this patent is extended or adjusted under 35 U.S.C. 154(b) by 0 days.

(21) Appl. No.: 15/319,126

(22) PCT Filed: Jun. 23, 2015

(86) PCT No.: PCT/KR2015/006372
§ 371 (c)(1),
(2) Date: Dec. 15, 2016

(87) PCT Pub. No.: WO2016/003104
PCT Pub. Date: Jan. 7, 2016

(65) Prior Publication Data
US 2017/0128351 A1    May 11, 2017

(30) Foreign Application Priority Data
Jun. 30, 2014  (KR) .................. 10-2014-0080987

(51) Int. Cl.
| A61K 8/891 | (2006.01) |
| A61K 8/365 | (2006.01) |
| A61K 8/02 | (2006.01) |
| A61K 8/25 | (2006.01) |
| A61K 8/58 | (2006.01) |
| A61K 8/81 | (2006.01) |
| A61Q 1/10 | (2006.01) |
| A61K 8/19 | (2006.01) |
| A61K 8/92 | (2006.01) |
| A61K 8/89 | (2006.01) |
| A61K 8/37 | (2006.01) |
| A61K 8/73 | (2006.01) |

(52) U.S. Cl.
CPC ............ *A61K 8/891* (2013.01); *A61K 8/0245* (2013.01); *A61K 8/19* (2013.01); *A61K 8/25* (2013.01); *A61K 8/365* (2013.01); *A61K 8/37* (2013.01); *A61K 8/58* (2013.01); *A61K 8/73* (2013.01); *A61K 8/8111* (2013.01); *A61K 8/89* (2013.01); *A61K 8/92* (2013.01); *A61K 8/927* (2013.01); *A61Q 1/10* (2013.01); *A61K 2800/412* (2013.01)

(58) Field of Classification Search
None
See application file for complete search history.

(56) References Cited

U.S. PATENT DOCUMENTS

| 5,750,127 A * | 5/1998 | Rokitowski ............ A61K 8/922 424/401 |
| 6,338,839 B1 | 1/2002 | Auguste et al. |
| 8,173,109 B2 | 5/2012 | Mori et al. |
| 2003/0017123 A1* | 1/2003 | Scancarella ............ A61K 8/06 424/63 |
| 2005/0271611 A1 | 12/2005 | Yoshida et al. |
| 2006/0257343 A1* | 11/2006 | Mori ........................ A61K 8/11 424/70.6 |
| 2008/0026016 A1* | 1/2008 | Koepsel ................. A61K 9/146 424/401 |

FOREIGN PATENT DOCUMENTS

| EP | 1649893 A1 | 4/2006 |
| JP | 2003055158 A | 2/2003 |
| JP | 2004315420 | 11/2004 |
| JP | 2005350368 | 12/2005 |
| JP | 2007269676 | 10/2007 |
| JP | 2013227277 A | 11/2013 |
| KR | 20000017236 A | 3/2000 |
| KR | 1020060128361 A | 12/2006 |
| KR | 1020100014314 A | 2/2010 |
| KR | 1020110049375 A | 5/2011 |
| KR | 101088624 B1 | 11/2011 |
| KR | 1020130122071 A | 11/2013 |
| WO | 2004087078 | 10/2004 |
| WO | 2008088323 A2 | 7/2008 |

OTHER PUBLICATIONS

"Cyclopentasiloxane," EWG's Skin Deep® Cosmetics Database, <https://www.ewg.org/skindeep/ingredient/701741/CYCLOPENTASILOXANE/#.WkwIOmaWw8R>, Copyright 2007-2018, p. 1-3.*
"Isopar E Fluid," Material Safety Data Sheet, Revision Date: Dec. 30, 2013, p. 1-12.*
ShinEtsu, "Silicone Proudcts for Personal Care," Shin-Etsu Silicone, published Jul. 2016, p. 1-16.*
Material Safety Data Sheet, "ISOPAR E," ExxonMobil Lubricants & Petroleum Specialties, Date Issued: Sep. 19, 2000, p. 1-7.*
Material Safety Data Sheet, "Isododecane," Print date: Mar. 31, 2011, p. 1-6.*

(Continued)

*Primary Examiner* — Monica A Shin
(74) *Attorney, Agent, or Firm* — Cantor Colburn LLP

(57) ABSTRACT

The present invention provides an eye make-up cosmetic composition containing a low-specific-gravity oil and a low-specific-gravity powder. The present invention provides an eye make-up cosmetic composition with excellent curling holding force, wherein the composition does not contain water and aqueous ingredients at all and contains a low-specific-gravity oil and a low-specific-gravity powder together, thereby allowing a formed curling force to be maintained as is, all day, when the composition is coated on hair such as the eyelashes.

11 Claims, No Drawings

(56) References Cited

OTHER PUBLICATIONS

International Search Report with English Translation for International Application No. PCT/KR2015/006372 dated Aug. 10, 2015.
Written Opinion for International Application No. PCT/KR2015/006372 dated Aug. 10, 2015.
Supplemental European Search Report for Application No. 15814310.7 dated Dec. 20, 2017.
Japanese Office Action—Japan Application No. 2016-574226 dated Nov. 13, 2018.
Japanese Office Action—Japan Application No. JP2016-574226 dated Jun. 3, 2019, citing references listed within.

* cited by examiner

EYE MAKE-UP COSMETIC COMPOSITION WITH EXCELLENT CURLING HOLDING FORCE

TECHNICAL FIELD

The present disclosure relates to a cosmetic composition having excellent curling retentivity to eyelashes.

BACKGROUND ART

Functional properties required for eye makeup cosmetics, such as mascara used for eyelashes, include voluming capability, curling capability and long lash formability. In addition, due to the climate that is gradually subjected to high temperature and high humidity, there has been an increasing need for long-term durability of the initial makeup state, i.e., curling retentivity by which the curling degree of eyelashes having makeup is maintained as it is for a long time without drooping, in addition to an effect of light eyelash makeup.

Thus, many attempts have been made to improve the curling retentivity of eye makeup cosmetics for use in eyelashes. However, it is difficult to provide excellent curling capability and voluming capability simultaneously with high curling retentivity. For example, Korean Laid-Open Patent No. 10-2006-0128361 discloses "Mascara composition containing hollow powder", wherein the hollow powder is organic resin powder such as acrylic acid, ester acrylate, methacrylic acid, ester methacrylate or acrylonitrile, which is differentiated from general inorganic powder. Herein, the hollow resin powder is hollow but does not necessarily have low specific gravity. In addition, the composition according to the related art is formed of an oil-in-water type composition containing a surfactant and water to realize voluming capability, and thus it has a specific gravity similar to or higher than the specific gravity of water, resulting in a problem of drooping of curling with time. Japanese Laid-Open Patent No. 2003-0055158 discloses "Mascara containing solid particles", the object of which is to improve curling capability by incorporating particles of silica, glass, diamond, boron nitride, ceramics, metal oxides, polyamide or a mixture thereof having a particle size of 5 nm-50 nm in addition to a volatile oil ingredient including hydrocarbon oil, silicone oil or a mixture thereof. However, since the mascara composition is one including not only water, an aqueous wax ingredient and an aqueous polymer ingredient but also a surfactant, it has a specific gravity higher than the specific gravity of water, resulting in a problem of degradation of curling retentivity by which the curling capability is maintained without drooping for a long time. In addition, the mascara composition also includes 0.1-30 wt % of non-volatile oil, which has a larger molecular weight, higher branching degree and higher viscosity as compared to volatile oil, resulting in interruption of rapid drying generally required for mascara and staining and spreading under the eye. Further, although the mascara composition contains ultramicro-powder having a particle size of 5 nm-50 nm, the specific gravity of powder is not related with the particle size but with the vacant space in the powder. Moreover, since powder having a size of 0.1 μm or less easily flies in the form of dust in the manufacturing environment, there is a possibility that the worker aspirates the dust.

REFERENCES

Patent Documents

Korean Laid-Open Patent No. 10-2006-0128361 (2006 Dec. 14)

Japanese Laid-Open Patent No. 2003-0055158 (2003 Feb. 26)

DISCLOSURE

Technical Problem

A technical problem to be solved by the present disclosure is to provide a cosmetic composition for eye makeup, which has excellent curling capability and formulation stability, while reducing the specific gravity of the overall composition, so that the problem of poor retentivity of a curling shape formed by applying an eye makeup composition to eyelashes or eyebrows with time may be overcome fundamentally. Particularly, a technical problem to be solved by the present disclosure is to provide a cosmetic composition for eye makeup, which shows excellent curling capability when applied to the hair, such as eyelashes, while maintaining the curling capability provided upon the application to the hair with no change even after the lapse of time so that any change in shape (curling) may be prevented fundamentally. Another technical problem to be solved by the present disclosure is to provide a cosmetic composition for eye makeup, which is dried rapidly upon the application so that the skin around the application site may not be contaminated with the content of cosmetic composition.

Technical Solution

In one general aspect, there is provided a cosmetic composition for eye makeup, which includes low-specific gravity volatile oil and low-specific gravity powder, wherein the specific gravity of each of the low-specific gravity volatile oil and the low-specific gravity powder is equal to or more than 0.001 and less than 1 when the specific gravity of the standard material, pure water at 4° C., is taken as 1.

Advantageous Effects

The cosmetic composition for eye makeup according to the embodiments of the present disclosure does not include water and aqueous ingredients but include volatile oil having a low specific gravity less than 1 and powder having a low specific gravity less than 1, and thus has a very low specific gravity as a whole. Therefore, when applying the cosmetic composition to the hair, such as eyelashes, it is possible to maintain the initial hair curling capability having makeup all day with no change by virtue of the lack of a weight feeling.

In addition, since the cosmetic composition for eye makeup according to the embodiments of the present disclosure does not include non-volatile oil but include low-specific gravity volatile oil, it is possible to realize a rapid drying speed, which is essentially required for cosmetic compositions for eye makeup. Therefore, the cosmetic composition for eye makeup causes no contamination around the eye when it is applied to the eyelashes, and maintains high curling capability at the initial application for a long time, and thus completes makeup requiring no supplementary makeup all day, once the makeup is applied to the user in the morning.

BEST MODE

As used herein, the term "hair" means a thread-like structure including keratin formed of keratinized epithelial cells and protruding out from the skin surface and is used in its broadest concept covering all of eyelashes, eyebrows and hair regardless of skin sites where hair grows, shapes of hair and functions of hair.

Hereinafter, the present disclosure will be explained in more detail.

In one aspect, there is provided a cosmetic composition for eye makeup, which includes low-specific gravity volatile oil and low-specific gravity powder, wherein the specific gravity of each of the low-specific gravity volatile oil and the low-specific gravity powder is equal to or more than 0.001 and less than 1, when the specific gravity of the standard material, pure water at 4° C., is taken as 1. The cosmetic composition for eye makeup according to an embodiment is a non-aqueous composition not including water or aqueous ingredients, and the composition containing the low-specific gravity volatile oil and low-specific gravity powder has a specific gravity less than 1, more particularly equal to or more than 0.001 and less than 1.

The specific gravity means a ratio of the mass of a given material to that of the standard material having the same volume of the given material. In the case of a liquid, the specific gravity of pure water at 4° C. as a standard material is taken as 1. Therefore, a specific gravity less than 1 means that the given material has a smaller weight as compared to water having the same volume, and as the value of specific gravity decreases, the mass of the corresponding material decreases.

As used herein, oil means a non-aqueous fatty material that is liquid at room temperature (25° C.) under ambient pressure (760 mmHg). According to an embodiment, the low-specific gravity oil means oil having a specific gravity less than 1. According to another embodiment, the low-specific gravity oil may have a low specific gravity equal to or more than 0.001 and less than 1, more particularly equal to or more than 0.1 and less than 1, for example. According to still another embodiment, the oil may be classified into volatile oil and non-volatile oil, and the volatile oil according to an embodiment of the present disclosure means oil that can evaporate at room temperature under ambient pressure within 1 hour upon the contact with the skin or keratin fibers.

The composition according to an embodiment of the present disclosure may include, as low-specific gravity volatile oil, at least one selected from the group consisting of low-specific gravity volatile hydrocarbon oil and low-specific gravity volatile silicone oil. The hydrocarbon oil is oil containing hydrogen and carbon atoms. Particular examples of the low-specific gravity volatile hydrocarbon oil according to an embodiment may include C8-C16 hydrocarbon oil. More particularly, the low-specific gravity volatile hydrocarbon oil may be C8-C16 branched alkanes, esters or a mixture thereof, and particular examples of the C8-C16 branched alkanes may include C8-C16 isoalkanes also known as isoparaffins, such as isodecane, isododecane or isohexadecane. The volatile silicone oil is volatile linear or cyclic silicone oil. The low-specific gravity volatile silicone oil according to an embodiment has a viscosity of 6 cst or less at 25° C. and particular examples thereof include silicone oil having 2-5 silicon atoms. More particularly, the low-specific gravity volatile silicone oil may include dimethicone, trisiloxane, cyclopentasiloxane or a mixture thereof.

The composition according to an embodiment of the present disclosure may include the low-specific gravity volatile oil in an amount of 1-80 wt %, more particularly 30-50 wt % based on the total weight of the composition. When the amount of the low-specific gravity volatile oil is less than 1 wt %, the amount of a solvent capable of dispersing solids is too small to make a cream-like formulation suitable for applications in eyelashes, and it is difficult to provide the resultant composition with low specific gravity. When the amount of the low-specific gravity volatile oil is larger than 80 wt %, evaporation occurs too fast, thereby making it difficult to prepare and store the composition.

The low-specific gravity powder according to an embodiment of the present disclosure means powder having a specific gravity less than 1. According to an embodiment, the low-specific gravity powder may have a specific gravity equal to or higher than 0.001 and less than 1, more particularly equal to or higher than 0.1 and less than 1. Particular examples of the low-specific gravity powder may include at least one selected from the group consisting of talc, sericite, mica, calcium carbonate, magnesium carbonate, kaolin, boron nitride, titanium dioxide, zinc oxide, iron oxide, carbon black, cerium oxide, zirconium oxide, silica, nylon and polymethyl methacrylate. When the powder has a specific gravity equal to or more than 1, the composition containing the powder shows a weight feeling when it is attached to the eyelashes and causes degradation of curling capability with time due to such a weight feeling.

According to an embodiment, the low-specific gravity powder may have a spherical shape, plate-like shape or needle-like shape, but is not limited thereto. In addition, the powder may have a porous or hollow shape having many vacant holes therein rather than a solid shape. The powder may have an average particle diameter of 20 μm or less, more particularly 0.1 μm or more and 20 μm or less, but is not limited thereto.

The composition according to an embodiment of the present disclosure may include the low-specific gravity powder in an amount of 0.1-20 wt %, more particularly 1-10 wt % based on the total weight of the composition. When the amount of the low-specific gravity powder is less than 0.1 wt %, it is not possible to obtain a sufficient effect of low specific gravity in the composition. When the amount of the low-specific gravity powder is larger than 20 wt %, the composition has increased viscosity and agglomerates in the form of clusters when it is applied to the eyelashes, resulting in a non-clear makeup state of eyelashes.

According to an embodiment, the composition may further include a dispersant. The composition according to the present disclosure contains neither water and aqueous ingredients nor surfactant ingredients. Thus, it is possible to disperse the low-specific gravity powder homogeneously in the low-specific gravity volatile oil and to prevent agglomeration of the composition by incorporating a dispersant to the composition, thereby improving the formulation stability. According to an embodiment, the dispersant may include at least one selected from the group consisting of polyhydroxystearic acid, lecithin, ethylhexylpalmitate, isopropylpalmitate, isostearic acid and polyglyceryl-3 polyricinoleate.

According to an embodiment, the composition may include the dispersant in an amount of 1-50 wt %, more particularly 3-30 wt %, based on the total weight of the low-specific gravity powder. When the amount of the dispersant is less than 1 wt %, there is little effect of dispersing powder, and thus the powder precipitates with the lapse of time and the resultant formulation becomes unstable. When the amount of the dispersant is larger than 50 wt %, there is no additional effect of dispersing powder, resulting in degradation of efficiency.

The cosmetic composition for eye makeup according to the embodiments of the present disclosure may further include wax, a thickening agent, preservative, plasticizer, or the like, in addition to the above ingredients, within such a range that does not adversely affect the objects and effects of the present disclosure.

In addition to the above active ingredients, the eye makeup composition according to the present disclosure may further include ingredients (also referred to as "other ingredients" hereinafter) used in conventional eye makeup compositions, such as wax, oil, powder, a thickening agent, pigment, film-forming agent, nutrients, volatile solubilizer, antioxidant, preservative and fragrance, within such a range that does not adversely affect the effects of the present disclosure.

Further, the eye makeup composition according to the present disclosure may be incorporated to formulations including mascara, eyeshadow, eyebrow pencils and eyeliners. Particularly, the eye makeup composition may be mascara, but is not limited thereto. According to another embodiment, the composition according to the present disclosure may be applied not only to eye makeup compositions but also to formulations for hair styling.

MODE FOR INVENTION

Hereinafter, the present disclosure will be explained with reference to the following examples. The following examples are for illustrative purposes only and not intended to limit the scope of the present disclosure.

In addition, it will be understood by those skilled in the art that various changes in form and details may be made thereto without departing from the scope of this disclosure as defined by the appended claims.

Examples 1-4 and Comparative Examples 1-3

Hereinafter, the mascara compositions according to some embodiments of the present disclosure, i.e. the compositions Examples 1-4 will be explained in terms of their compositions and preparation. In addition, to explain the properties of the inventive examples more clearly, Comparative Examples 1-3 are prepared according to the conventional mascara composition by the conventional method and compared with the inventive examples.

The following Table 1 shows the compositions of Examples 1-4 according to the present disclosure and those of Comparative Examples 1-3.

TABLE 1

| Ingredients (unit: wt %) | Comp. Ex. 1 | Comp. Ex. 2 | Comp. Ex. 3 | Ex. 1 | Ex. 2 | Ex. 3 | Ex. 4 |
|---|---|---|---|---|---|---|---|
| 1. Polyethylene | 5.0 | 5.0 | 5.0 | 5.0 | 5.0 | 5.0 | 5.0 |
| 2. Microcrystalline wax | 5.0 | 5.0 | 5.0 | 5.0 | 5.0 | 5.0 | 5.0 |
| 3. Bees wax | 5.0 | 5.0 | 5.0 | 5.0 | 5.0 | 5.0 | 5.0 |
| 4. Polyisobutene | 5.0 | 5.0 | 5.0 | 5.0 | 5.0 | 5.0 | 5.0 |
| 5. Disteadimonium hectorite | 5.0 | 5.0 | 5.0 | 5.0 | 5.0 | 5.0 | 5.0 |
| 6. Propylene carbonate | 3.0 | 3.0 | 3.0 | 3.0 | 3.0 | 3.0 | 3.0 |
| 7. Dextrin palmitate | 2.0 | 2.0 | 2.0 | 2.0 | 2.0 | 2.0 | 2.0 |
| 8. Cetyl PEG/PPG-10/1 dimethicone | 3.0 | 3.0 | — | — | — | — | — |
| 9. Trimethylsiloxysilicate | 10.0 | 10.0 | 10.0 | 10.0 | 10.0 | 10.0 | 10.0 |
| 10. Polyhydroxystearic acid | — | — | — | — | 1.0 | 1.0 | 2.0 |
| 11. Low-specific gravity non-volatile - dimethicone (specific gravity 0.98, viscosity 20cs) | 30.0 | — | 51.5 | — | — | — | — |
| 12. Low-specific gravity volatile - dimethicone (specific gravity 0.85, viscosity 1.5cs) | — | 30.0 | — | 51.5 | 50.5 | — | 20.0 |
| 13. Low-specific gravity - isododecane (specific gravity 0.8, viscosity 1cs) | — | — | — | — | — | 50.5 | 29.5 |
| 14. Black iron oxide (specific gravity 3.0, size 1 μm) | 8.0 | — | — | — | — | — | — |
| 15. Low-specific gravity carbon black (specific gravity 0.2, size 0.1 μm) | — | 3.0 | 3.0 | 3.0 | 3.0 | 3.0 | 3.0 |
| 16. Silica (specific gravity 1.8, size 5 μm) | 5.0 | — | — | — | — | — | — |
| 17. Low-specific gravity - silica (specific gravity 0.8, size 5 μm) | — | 5.0 | 5.0 | 5.0 | 5.0 | 5.0 | 2.5 |
| 18. Low-specific gravity - talc (specific gravity 0.85, size 5 μm) | — | — | — | — | — | — | 2.5 |
| 19. Water | 13.0 | 18.0 | — | — | — | — | — |
| 20. Sodium hydroxide | 0.5 | 0.5 | — | — | — | — | — |
| 21. Preservative | 0.5 | 0.5 | 0.5 | 0.5 | 0.5 | 0.5 | 0.5 |

Method for Preparing Comparative Examples 1 and 2

1) Ingredients 1-13 are heated to 90° C. and dissolved.
2) Ingredients 19-20 are heated to 90° C. and dissolved.
3) Ingredients 14-18 are added gradually to the above 1) and mixed under agitation.
4) The above 2) is added gradually to the above 3) to perform emulsification.
5) After the emulsification, Ingredient 21 is added to the above 4), while cooling them to 30° C.
6) The resultant product is filled into a mascara container.

Method for Preparing Comparative Example 3 and Examples 1-4

1) Ingredients 1-13 are heated to 90° C. and dissolved.
2) Ingredients 14-18 are added gradually to the above 1) and mixed under agitation.
3) Ingredient 21 is added to the above 2), while cooling them to 30° C.
4) The resultant product is filled into a mascara container.

[Test Example 1] Test of Feel of Use (Sensory Evaluation)

Thirty females of 20-40 ages using mascara every day or frequently are allowed to use the mascara products of Comparative Examples 1-3 obtained by the conventional method and those of Examples 1-4 obtained by the method according to the present disclosure, and then to compare the effects of Comparative Examples with those of Examples. The test items include lightness, curling capability, curling retentivity, drying speed and lack of agglomeration. Each user is allowed to evaluate each product in terms of each test item and to classify it into grade from 0 to 15, and then the grades are averaged. To increase the accuracy of data, each test is repeated five times. The results are shown in the following Table 2. An average less than 4.0 is represented by "X", an average of 4.0-8.0 is represented by "Δ", an average of 8.1-12.0 is represented by "○", and an average greater than 12.0 is represented by "◎".

TABLE 2

| Test Items | Comp. Ex. 1 | Comp. Ex. 2 | Comp. Ex. 3 | Ex. 1 | Ex. 2 | Ex. 3 | Ex. 4 |
| --- | --- | --- | --- | --- | --- | --- | --- |
| Lightness | X | Δ | Δ | ◎ | ◎ | ◎ | ◎ |
| Curling capability | ○ | ◎ | ○ | ◎ | ◎ | ◎ | ◎ |
| Curling retentivity | X | X | Δ | ○ | ○ | ◎ | ◎ |
| Drying speed | Δ | Δ | X | ○ | ○ | ◎ | ○ |
| Lack of agglomeration | ○ | ○ | Δ | Δ | ○ | ○ | ◎ |

As can be seen from Table 2, the conventional mascara compositions of Comparative Examples 1 and 2 containing water and aqueous ingredients show a lower grade in terms of lightness, curling retentivity and drying speed, as compared to Comparative Example 3 not containing water and aqueous ingredients and the compositions of Examples 1-4 according to the present disclosure. This is because a formulation containing water and aqueous ingredients has a specific gravity similar to or higher than the specific gravity of water, and thus the formulation causes a weight feeling and drooping of curling at the eyelashes. In addition, Comparative Example 3 not containing water and aqueous ingredients but containing low-specific gravity non-volatile oil and low-specific gravity powder provides slightly improved lightness and curling retentivity but shows the lowest degree of satisfaction in terms of drying speed due to the soft and sticky feel of non-volatile oil. On the contrary, Examples 1-4 containing both low-specific gravity volatile oil and low-specific gravity powder according to the present disclosure provides a significantly improved degree of satisfaction in terms of lightness and curling retentivity as compared to the conventional compositions according to Comparative Examples.

Referring to the item of lack of agglomeration, Comparative Example 3 and Example 1 containing no surfactant and additional dispersants provide a lower degree of satisfaction as compared to Comparative Examples 1 and 2 containing a surfactant and Examples 2-4 containing additional dispersants.

[Test Example 2] Determination of Specific Gravity

The following method is used to determine the specific gravity data of mascara obtained from each of the compositions according to Comparative Examples 1-3 and Examples 1-4.

Method for Determining Specific Gravity

1) A 50 ml specific gravity cup is prepared and weighed.
2) The specific gravity cup is completely filled with water and then weighed.
3) The weight of specific gravity cup is subtracted from the weight of specific gravity cup+water to obtain the weight of water.
4) The specific gravity cup of the above 1) is completely filled with each composition and then weighed.
5) The weight of specific gravity cup is subtracted from the weight of specific gravity cup+composition to obtain the weight of composition.
6) The weight of composition is divided by the weight of water to obtain the specific gravity of composition.

The above test is repeated three times for each composition and the results are averaged. The results are shown in the following Table 3.

TABLE 3

| Test Item | Comp. Ex. 1 | Comp. Ex. 2 | Comp. Ex. 3 | Ex. 1 | Ex. 2 | Ex. 3 | Ex. 4 |
| --- | --- | --- | --- | --- | --- | --- | --- |
| Specific gravity | 1.10 | 1.04 | 1.02 | 0.91 | 0.91 | 0.75 | 0.80 |

As can be seen from Table 3, Examples 1-4 according to the present disclosure have a specific gravity less than 1, which is lower than the specific gravity of each of the conventional mascara compositions according to Comparative Examples 1-3. This is because the composition according to the present disclosure does not contain water and aqueous ingredients but contains low-specific gravity volatile oil and low-specific gravity powder at the same time, resulting in a decrease in specific gravity of composition. In this manner, the composition according to the present disclosure provides excellent lightness and positively affects curling retentivity by causing no degradation in curling degree upon the application to the eyelashes and maintaining the curling degree as it is. As the specific gravity of volatile oil decreases and that of powder decreases, the specific gravity of composition also decreases, resulting in improvement of curling retentivity.

[Test Example 3] Test of Dispersability

The following method is used to determine the dispersability of mascara obtained from each of the compositions according to Comparative Examples 1-3 and Examples 1-4. A centrifugal system is used to separate liquid ingredients from solid ingredients and the separated liquid phase is determined for its height. Herein, as the height of the separated liquid phase increases, the formulation stability decreases.

Method for Determining Dispersability

1) Each of the compositions is introduced into a tube in a centrifugal system in the same amount of 15 g.
2) The centrifugal system is operated under 1000 rpm for 5 minutes.
3) The tube is taken out and the height of the separated liquid phase is determined.

Each composition is tested three times and the results are averaged. The results are shown in the following Table 4.

TABLE 4

| Test Item | Comp. Ex. 1 | Comp. Ex. 2 | Comp. Ex. 3 | Ex. 1 | Ex. 2 | Ex. 3 | Ex. 4 |
|---|---|---|---|---|---|---|---|
| Height of separated layer (mm) | 11.0 | 11.0 | 25.5 | 24.0 | 10.5 | 11.0 | 9.0 |

As can be seen from Table 4, the conventional compositions according to Comparative Examples 1-2 contains a surfactant to form an oil-in-water type emulsion formulation in addition to water and aqueous ingredients, and thus the surfactant also functions as a dispersant for powder. As a result, the conventional compositions provide stable formulations having a low separation height in a centrifugal system. However, Comparative Example 3 and Example 1 containing no additional dispersant causes a significantly large amount of oil separation in a centrifugal separation system. This is because separation of oil from powder proceeds in the formulation with time, resulting in degradation of the formulation stability. On the contrary, the compositions of Examples 2-4 according to the present disclosure contain a dispersant and provide a lower separation height in a centrifugal system, suggesting that they have excellent formulation stability.

[Test Example 4] Determination of Drying Speed

The following method is used to determine the drying time of mascara obtained from each of the compositions according to Comparative Examples 1-3 and Examples 1-4. As the complete drying time increases, the drying speed is low.

Method for Determining Drying Time

1) Each composition is applied to a glass plate by using an applicator to a thickness of 100 μm.
2) A filter paper is used to compress the application surface at an interval of 1 minute.
3) The time where the filter paper is not contaminated with the contents of composition any longer is determined.

Each composition is tested three times repeatedly and the results are averaged. The results are shown in the following Table 5.

TABLE 5

| Test Item | Comp. Ex. 1 | Comp. Ex. 2 | Comp. Ex. 3 | Ex. 1 | Ex. 2 | Ex. 3 | Ex. 4 |
|---|---|---|---|---|---|---|---|
| Complete drying time (min.) | 7.8 | 7.8 | 9.1 | 6.1 | 6.0 | 5.2 | 6.2 |

As can be seen from Table 5, Comparative Examples 1-2 containing to water and aqueous ingredients and Comparative Example 3 containing non-volatile oil show a drying time significantly lower than the drying time of Examples 1-4 containing volatile oil according to the present disclosure. Since a rapid drying speed is very important in view of properties of mascara, it can be seen that the inventive Examples are convenient to use.

[Test Example 5] Determination of Curling Retentivity

The following method is used to determine the curling retentivity of mascara obtained from each of the compositions according to Comparative Examples 1-3 and Examples 1-4. A digital camera is used to determine a change in curling angle with time. A smaller change in curling angle means higher curling retentivity.

Method for Determining Curling Retentivity

1) An artificial eyelash is attached to a semi-circular acrylic bar.
2) The position of digital camera is fixed so that the lateral side of artificial eyelash may be photographed.
3) Each composition is applied to the artificial eyelash 12 times in the same amount.
4) The curling angle of eyelash is determined with the digital camera right after the application.
5) Determination of the curling angle of eyelash is repeated by using the digital camera at an interval of 12 hours.

The test is repeated three times for each of the compositions according to Comparative Examples 1-3 and Examples 1-4 and the results are averaged. The results are shown in the following Table 6.

TABLE 6

| Test Item | Comp. Ex. 1 | Comp. Ex. 2 | Comp. Ex. 3 | Ex. 1 | Ex. 2 | Ex. 3 | Ex. 4 |
|---|---|---|---|---|---|---|---|
| Curling angle right after application (°) | 38.5 | 38.0 | 38.2 | 38.4 | 38.0 | 38.5 | 38.5 |
| Curling angle after 12 hours (°) | 22.2 | 25.0 | 29.7 | 36.7 | 36.4 | 37.0 | 37.0 |
| Curling angle after 24 hours (°) | 17.7 | 20.4 | 22.6 | 35.8 | 36.0 | 36.1 | 36.0 |

TABLE 6-continued

| Test Item | Comp. Ex. 1 | Comp. Ex. 2 | Comp. Ex. 3 | Ex. 1 | Ex. 2 | Ex. 3 | Ex. 4 |
|---|---|---|---|---|---|---|---|
| Curling angle after 50 hours (°) | 14.8 | 16.1 | 19.9 | 35.2 | 35.0 | 36.0 | 35.8 |

As can be seen from Table 6, the conventional mascara compositions of Comparative Examples 1-3 causes a rapid decrease in curling degree by at least 60% with time, while Examples 1-4 according to the present disclosure causes little difference between the curling angle right after the application and the curling angle after 36 hours. This suggests that the composition according to the present disclosure provides excellent curling retentivity. This is because the composition according to the present disclosure does not contain water and aqueous ingredients but contains low-specific gravity volatile oil and low-specific gravity powder at the same time, and thus it has low specific gravity and imparts a low weight feeling to the eyelashes, thereby reducing a phenomenon of drooping at the eyelashes caused by such a weight feeling with the lapse of time.

The invention claimed is:

1. A cosmetic composition for eye makeup, which comprises low-specific gravity volatile oil and low-specific gravity powder, and a dispersant,
    wherein the low-specific gravity volatile oil comprises low-specific gravity hydrocarbon oil and low-specific gravity volatile silicone oil,
    wherein a specific gravity of the low-specific gravity hydrocarbon oil is equal to or more than 0.1 and equal to or less than 0.8, and a specific gravity of the low-specific gravity silicone oil is equal to or more than 0.1 and equal to or less than 0.85, and the specific gravity of the low-specific gravity powder is equal to or more than 0.001 and less than 1, when the specific gravity of the standard material, pure water at 4° C., is taken as 1, wherein the composition is a non-aqueous composition not comprising water or aqueous ingredients.

2. The cosmetic composition for eye makeup according to claim 1, wherein the low-specific gravity volatile hydrocarbon oil is a C8-C16 branched alkane, ester or a mixture thereof.

3. The cosmetic composition for eye makeup according to claim 1, wherein the low-specific gravity volatile silicone oil is dimethicone, trisiloxane, or a mixture thereof.

4. The cosmetic composition for eye makeup according to claim 1, which comprises the low-specific gravity volatile oil in an amount of 1-80 wt % based on the total weight of the composition.

5. The cosmetic composition for eye makeup according to claim 1, wherein the low-specific gravity powder comprises at least one selected from the group consisting of talc, sericite, mica, calcium carbonate, magnesium carbonate, kaolin, boron nitride, titanium dioxide, zinc oxide, iron oxide, carbon black, cerium oxide, zirconium oxide, silica, nylon and polymethyl methacrylate.

6. The cosmetic composition for eye makeup according to claim 1, wherein the low-specific gravity powder has at least one shape selected from a spherical shape, plate-like shape and a needle-like shape, and has an average particle diameter of 0.1-20 μm.

7. The cosmetic composition for eye makeup according to claim 1, which comprises the low-specific gravity powder in an amount of 0.1-20 wt % based on the total weight of the composition.

8. The cosmetic composition for eye makeup according to claim 1, which has a specific gravity equal to or more than 0.001 and less than 1 as a whole.

9. The cosmetic composition for eye makeup according to claim 1, wherein the dispersant comprises at least one selected from the group consisting of polyhydroxystearic acid, lecithin, ethylhexylpalmitate, isopropylpalmitate, isostearic acid and polyglyceryl-3 polyricinoleate.

10. The cosmetic composition for eye makeup according to claim 1, which comprises the dispersant in an amount of 1-50 wt % based on the total weight of the low-specific gravity powder.

11. The cosmetic composition for eye makeup according to claim 1, which is for use in mascara.

* * * * *